(12) United States Patent
Lara-Montalvo et al.

(10) Patent No.: US 7,532,748 B2
(45) Date of Patent: May 12, 2009

(54) METHODS AND APPARATUS FOR SELECTING AND/OR LABELING VESSEL BRANCHES

(75) Inventors: Ruben Angel Lara-Montalvo, Paris (FR); Laurent Stefani, Paris (FR); Laurent Launay, St. Remy le Chevreuse (FR); Jérôme François Knoplioch, Neuilly sur Seine (FR)

(73) Assignee: General Electric Company, Schenectady, NY (US)

( * ) Notice: Subject to any disclaimer, the term of this patent is extended or adjusted under 35 U.S.C. 154(b) by 653 days.

(21) Appl. No.: 11/282,150

(22) Filed: Nov. 17, 2005

(65) Prior Publication Data

US 2006/0122501 A1 Jun. 8, 2006

Related U.S. Application Data

(60) Provisional application No. 60/630,884, filed on Nov. 24, 2004.

(51) Int. Cl.
*G06K 9/00* (2006.01)
*A61B 6/00* (2006.01)
(52) U.S. Cl. .......................... 382/131; 382/154; 378/21
(58) Field of Classification Search ................. 382/100, 382/128, 129, 130, 131, 132, 133, 134, 154, 382/168, 181, 184, 189, 191, 193–194, 199, 382/232, 243, 254, 260, 274, 276, 285, 287, 382/305, 312; 600/425, 426; 378/21, 23
See application file for complete search history.

(56) References Cited

U.S. PATENT DOCUMENTS

| 5,799,649 | A | 9/1998 | Prince |
| 6,662,038 | B2 | 12/2003 | Prince |
| 6,842,638 | B1 * | 1/2005 | Suri et al. .................... 600/425 |
| 6,999,811 | B2 * | 2/2006 | Koppe et al. ................. 600/426 |
| 7,113,623 | B2 * | 9/2006 | Chen et al. ................... 382/128 |
| 7,197,170 | B2 * | 3/2007 | Dwyer et al. ................ 382/128 |
| 7,203,354 | B2 * | 4/2007 | Wilson et al. ................ 382/131 |
| 7,343,029 | B2 | 3/2008 | Lienard et al. |
| 7,372,983 | B2 | 5/2008 | Bruijns |
| 7,397,942 | B2 * | 7/2008 | Bruijns ........................ 382/154 |

* cited by examiner

*Primary Examiner*—Seyed Azarian
(74) *Attorney, Agent, or Firm*—Armstrong Teasdale LLP

(57) ABSTRACT

A method for selecting and/or labeling a vessel image includes operating an imaging system to obtain reconstructed image data including a volume having vessels therein. A bone removal routine is then applied to the reconstructed image data to produce a bone-free image. An initial point on a main vessel in the bone-free image is located, and bifurcation points and branches departing from the main vessel are identified. An adjacency graph of each branch coming from the main vessel is built. The method includes either or both of selecting and displaying a best or at least a favorable path through the vessels in accordance with predetermined criteria using the adjacency branch, or labeling and displaying branches of the main vessel.

17 Claims, 9 Drawing Sheets

METHODS AND APPARATUS FOR SELECTING AND/OR LABELING VESSEL BRANCHES

CROSS REFERENCE TO RELATED APPLICATIONS

This application claims the benefit of U.S. Provisional App. No. 60/630,884, filed Nov. 24, 2004, entitled "Methods and apparatus for selecting and/or labeling vessel branches," which is hereby incorporated by reference in its entirety.

BACKGROUND OF THE INVENTION

This invention relates generally to methods and apparatus for analyzing and displaying vessel branches.

Identification and labeling of the different branches of a vessel from computed tomographic (CT) images is a routine task that can take precious time that can be better used for analysis and diagnosis of such vessels.

A known procedure for labeling and analyzing vessel branches includes manually positioning a point on an image of each of the branch ends utilizing a computer having a display and a user pointing device such as a mouse, trackball, or keyboard keys. After this selection, the computer executes a program that displays each vessel branch for diagnostic purposes.

For example, a CT image is selected from different aorta branches (e.g., celiac trunk, superior mesenteric artery, right renal, left renal, right external iliac, and/or left external iliac). Points are positioned in 2D image slices or in 3D images. A user positions a starting point with a pointing device and identifies each branch by positioning a point at extremities of the branch. After all the points have been positioned, the computer executes an auto-tracking software routine. This routine joins the starting point to the rest of the branch points, following a path inside the vessels.

Each branch is then displayed in different views (namely, 3D, lumen, axial, and oblique views) for vessel analysis. These views supply quantitative vessel information such as minimum and maximum diameter and facilitate the application of measurements to the images.

This manual procedure is relatively time consuming, especially for an untrained user. Moreover, the procedure does not always produce optimum results because it is difficult to manually position points at the precise extremities of a vessel branch. As a result, such vessel branches may be incompletely displayed.

BRIEF DESCRIPTION OF THE INVENTION

Therefore, some configurations of the present invention provide a method for selecting and/or labeling a vessel image. The method includes locating an initial point on a main vessel in a bone-free medical image obtained from a medical imaging apparatus and identifying bifurcation points and branches departing from the main vessel. The method further includes building an adjacency graph of each branch coming from the main vessel. The method also includes either or both of selecting and displaying a best or at least a favorable path through the vessels in accordance with predetermined criteria using the adjacency branch, or labeling and displaying branches of the main vessel.

In still another aspect, some configurations of the present invention provide a computer or workstation. The computer or workstation is configured to locate an initial point on a main vessel in a bone-free medical image obtained from a medical imaging apparatus, identify bifurcation points and branches departing from the main vessel, and build an adjacency graph of each branch coming from the main vessel. The computer or workstation is also configured to select and display a best or at least a favorable path through the vessels in accordance with predetermined criteria using the adjacency branch and/or label and display branches of the main vessel.

In yet another aspect, some configurations of the present invention provide a machine readable medium or media having recorded thereon instructions configured to instruct a processor to locate an initial point on a main vessel in a bone-free medical image obtained from a medical imaging apparatus and identify bifurcation points and branches departing from the main vessel. The instructions also include instructions configured to instruct the processor to build an adjacency graph of each branch coming from the main vessel. Also included are instructions configured to instruct the processor to select and display a best or at least a favorable path through the vessels in accordance with predetermined criteria using the adjacency branch and/or label and display branches of the main vessel.

Configurations of the present invention will be seen to provide rapid, automated identification and labeling of different branches of a CT image without requiring manual positioning of points.

DETAILED DESCRIPTION OF THE INVENTION

Figure 1:
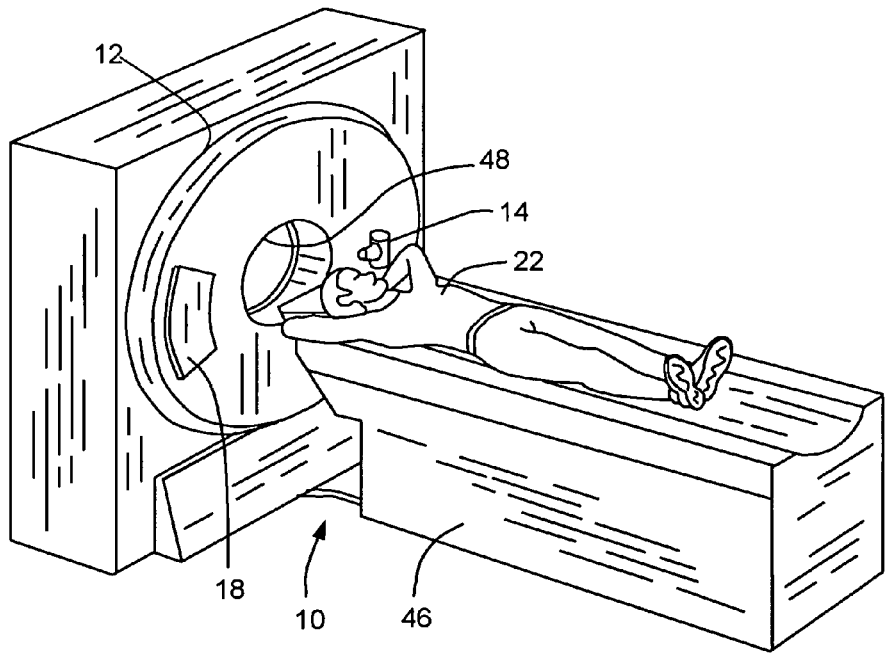
FIG. 1 is a pictorial representation of a medical imaging system, more particularly a computed tomographic imaging system.

Technical effects of some configurations of the present invention include providing an automated workflow that provides a visualization of branches in the aorta. Also, some configurations of the present invention provide automated analysis of other vessels such as coronary vessels. The automated workflow in some configurations provides or facilitates bone removal from a 3D CT image, volume analysis to accurately determine a starting point a distal point for each branch of an artery, and a tree analysis to display a central line and vessel quantifications (i.e., minimum and maximum diameters). Bone removal is provided in some configurations of the present invention using a known "auto bone" routine and tree analysis is provided by a known auto tracking routine.

Some configurations of the present invention utilize a volume analysis routine that accepts as input a vessel tree volume (from which bones and air have been removed) and produces as output distal points of all branches. These branches are also labeled. For example, a branch may be labeled as belong to the iliac or the renal artery, etc.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment," "one configuration," or "some configurations" of the present invention or similar references are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image, and the production of a displayed and viewable image is a technical effect of some configurations of the present invention.

Figure 2:
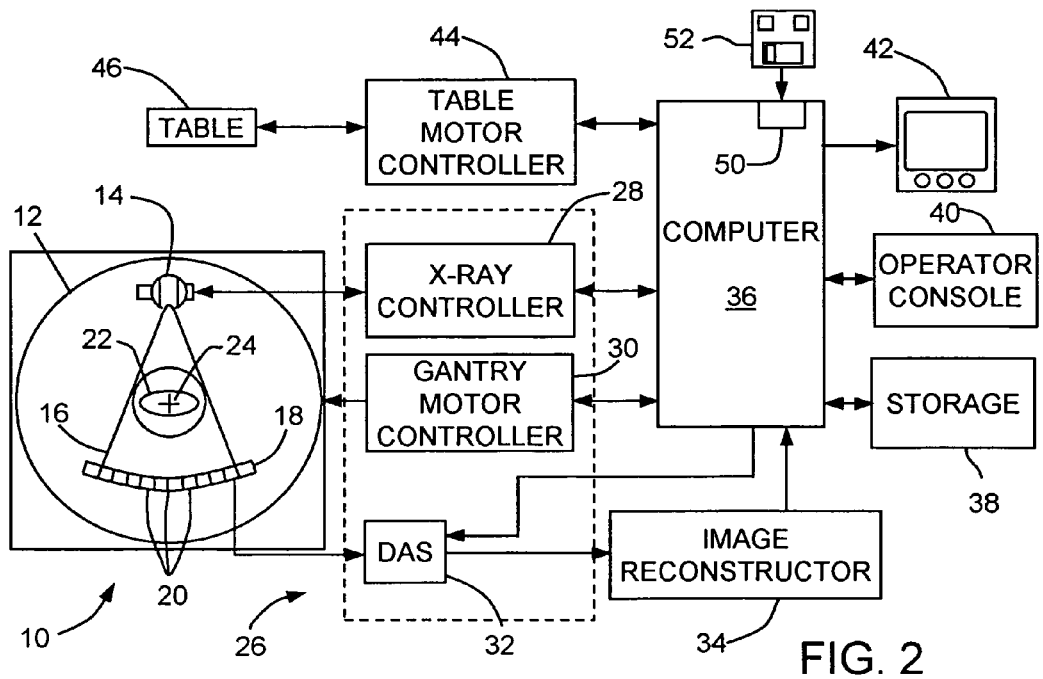
FIG. 2 is a pictorial block diagram of the medical imaging system of FIG. 1.

FIG. 1 is a pictorial view of a CT imaging system 10. FIG. 2 is a block schematic diagram of system 10 illustrated in FIG. 1. In some configurations of the present invention, a computed tomography (CT) imaging system 10 is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard and/or a pointing device, such as a mouse. An associated cathode ray tube display or other suitable display device 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems or with stand-alone computer systems and workstations or networked workstations. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

Figure 3:
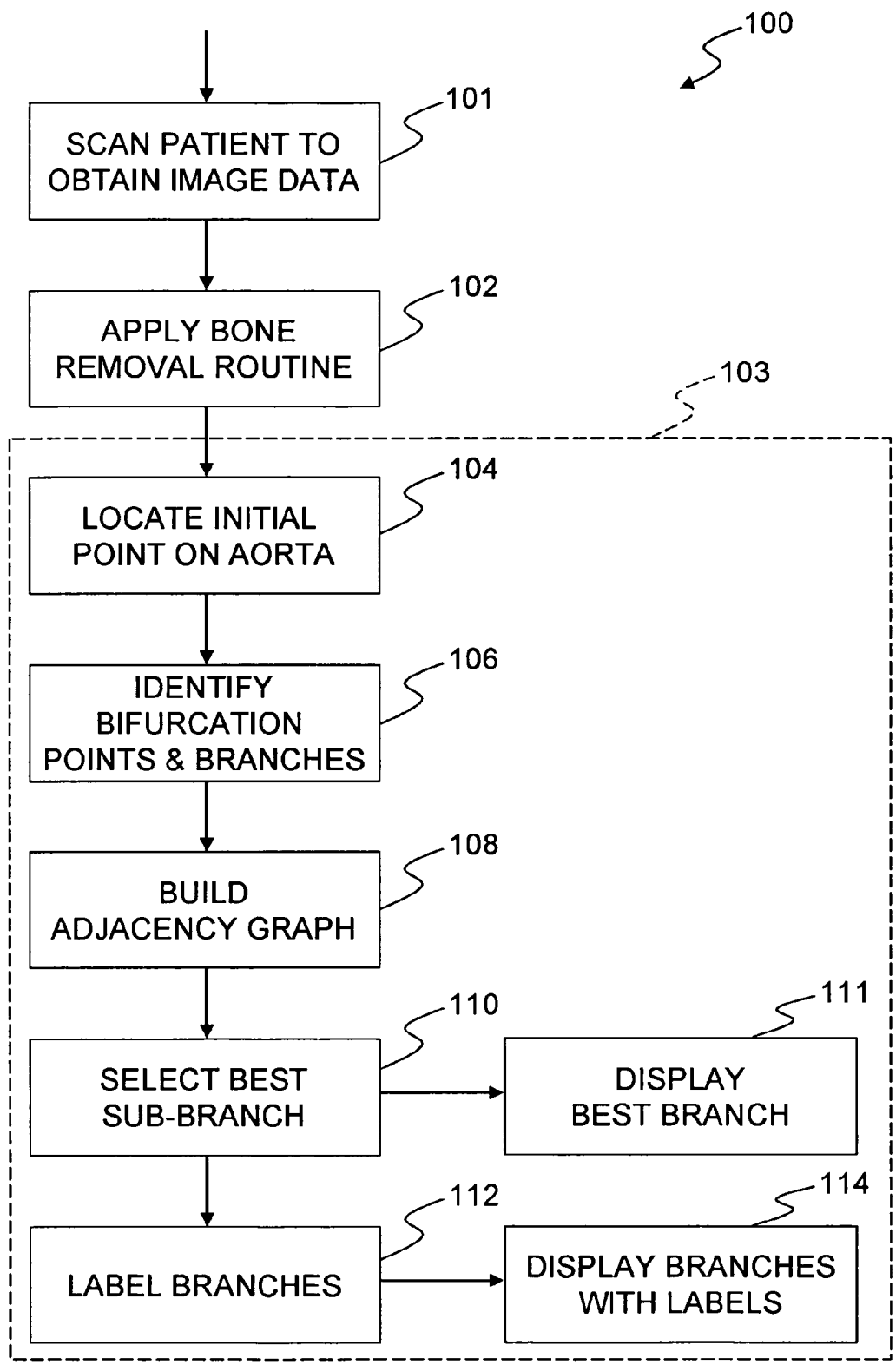
FIG. 3 is a flow chart representative of a method performed for selecting, labeling and displaying vessel branches in some configurations of the present invention.
Figure 4:
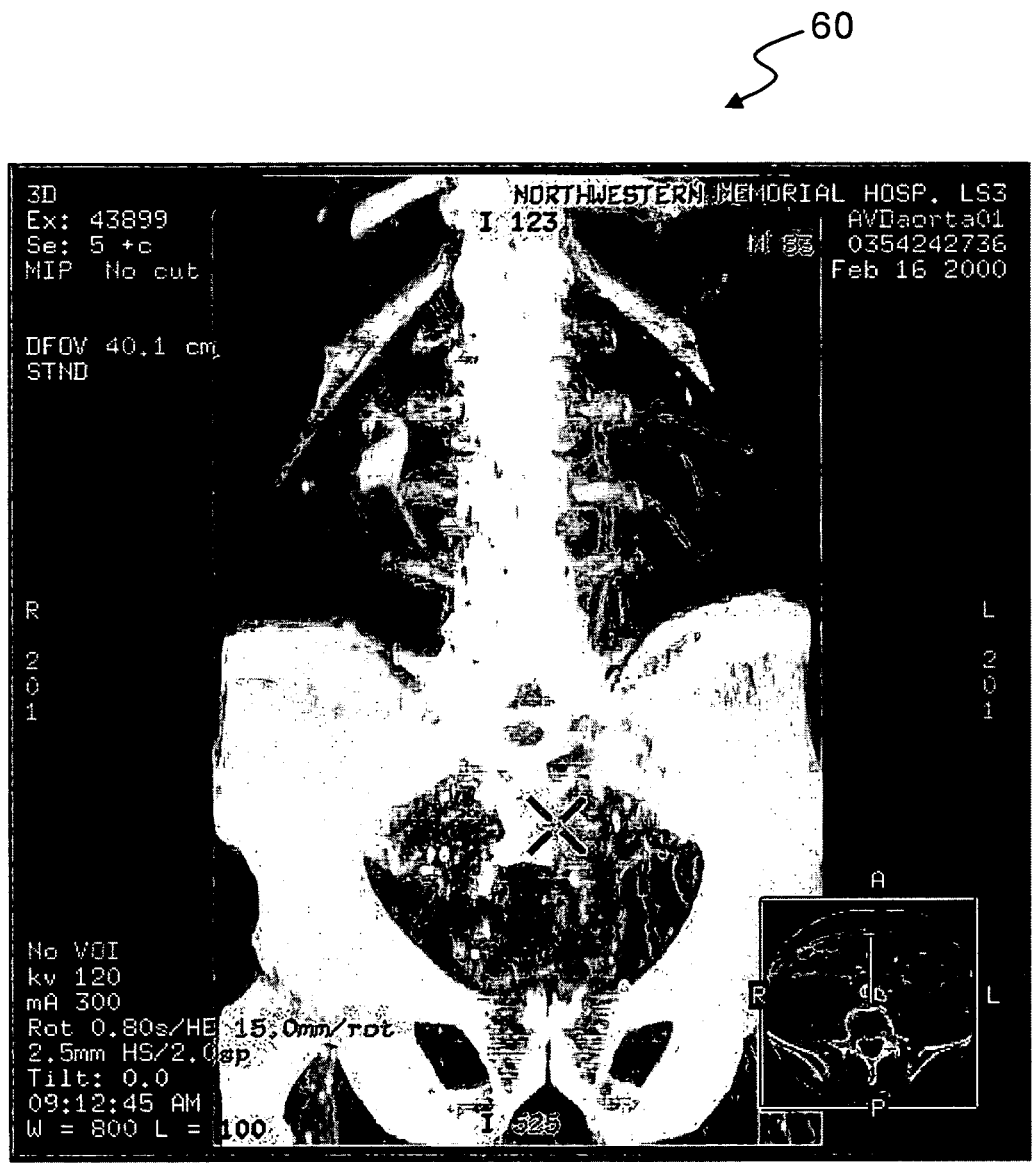
FIG. 4 is an example of a 3D CT abdominal image produced by the imaging system of FIG. 1 in a step represented in the flow chart of FIG. 3.
Figure 5:
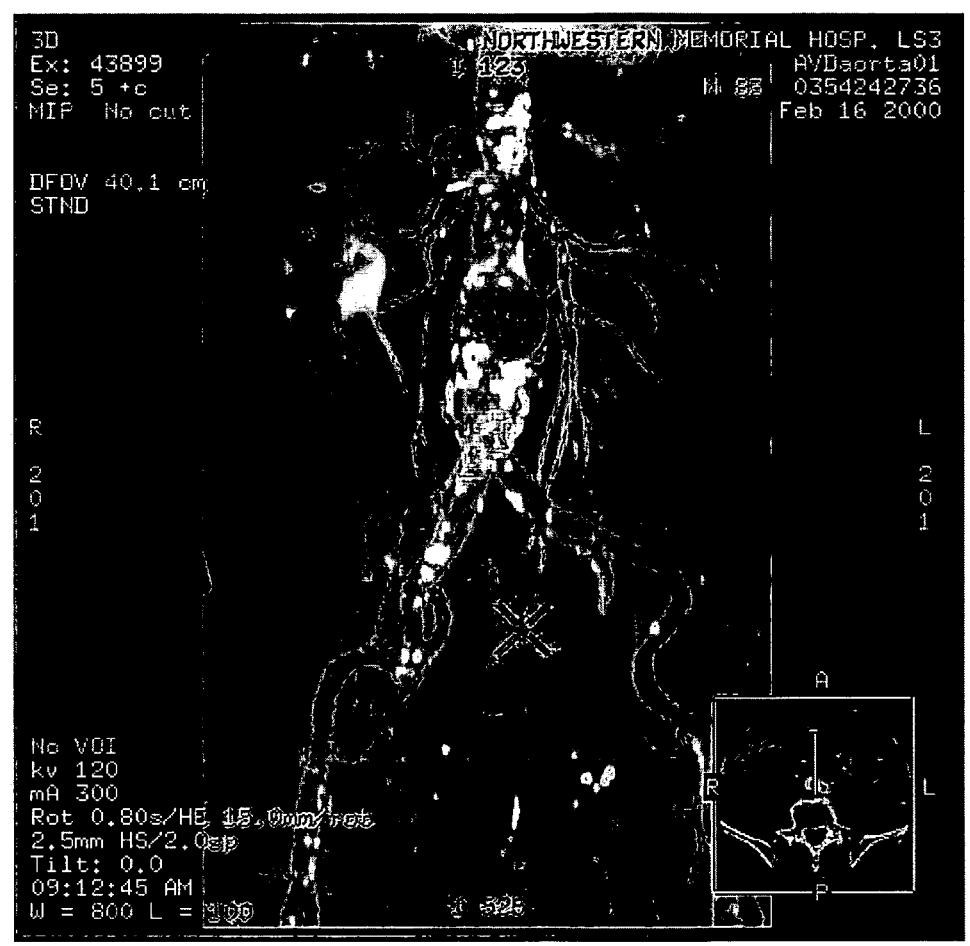
FIG. 5 is a bone free image produced from the image of FIG. 4.

In some configurations of the present invention and referring to flow chart 100 of FIG. 3, a technical effect of the present invention is achieved by an operator first scanning a patient 22 with imaging system 10 to obtain reconstructed image data including an aorta volume at step 101. (An aorta volume is recited here because the example presented herein concerns selecting and labeling aorta vessels. For example, if other vessels were to be selected and/or labeled, a volume appropriate to these other vessels would be scanned.) An example of a 3D CT abdominal image 60 produced by step 101 is shown in FIG. 4. At step 102, any known suitable bone removal routine is used to produce a bone free image 62, such as that shown in FIG. 5. Next, at step 104, volume analysis routine 103 locates an initial point on an aorta 64 (or another main vessel, as appropriate). More particularly, finding the initial point at step 104 is performed in some configurations from a "clean" aorta (without other small objects around it) by finding the highest 2D slice of the aorta and searching for the biggest connected component. The initial point is the center of this connected component.

Figure 6:
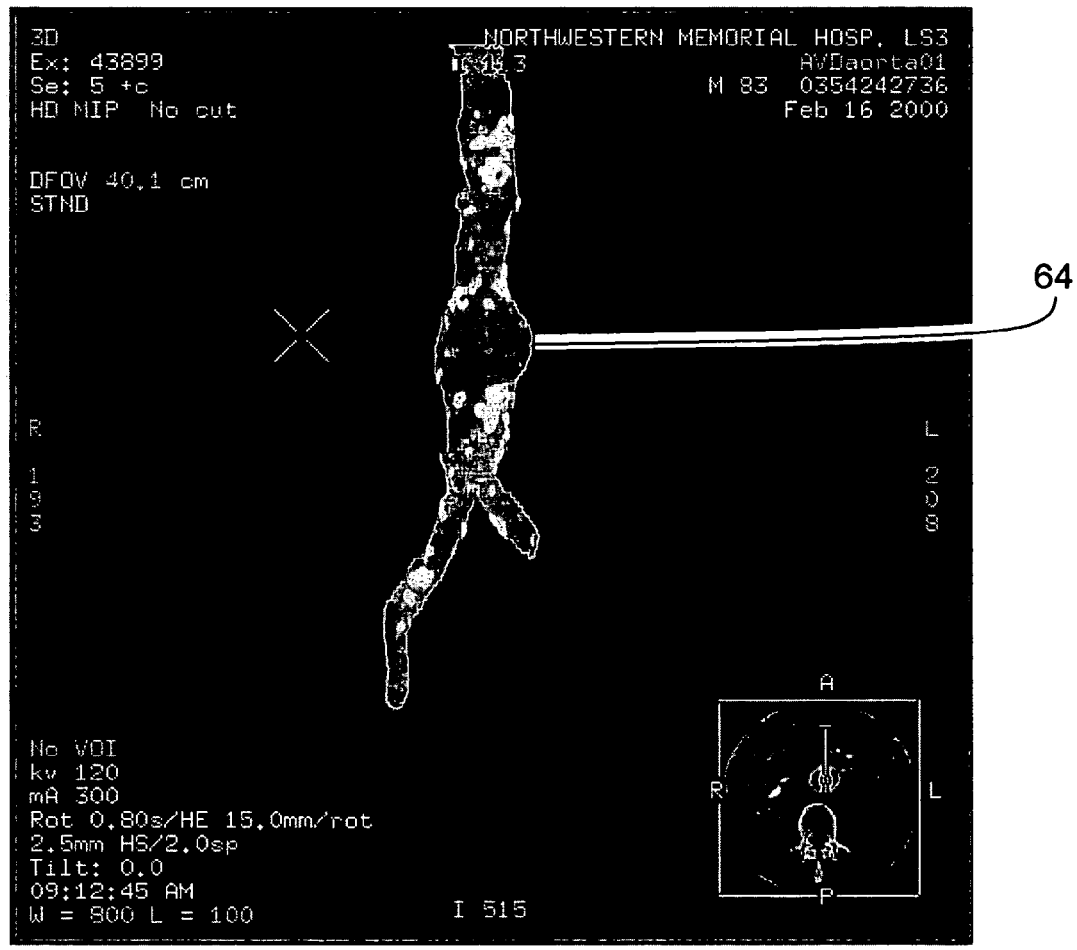
FIG. 6 is an image of a main aorta.
Figure 7:
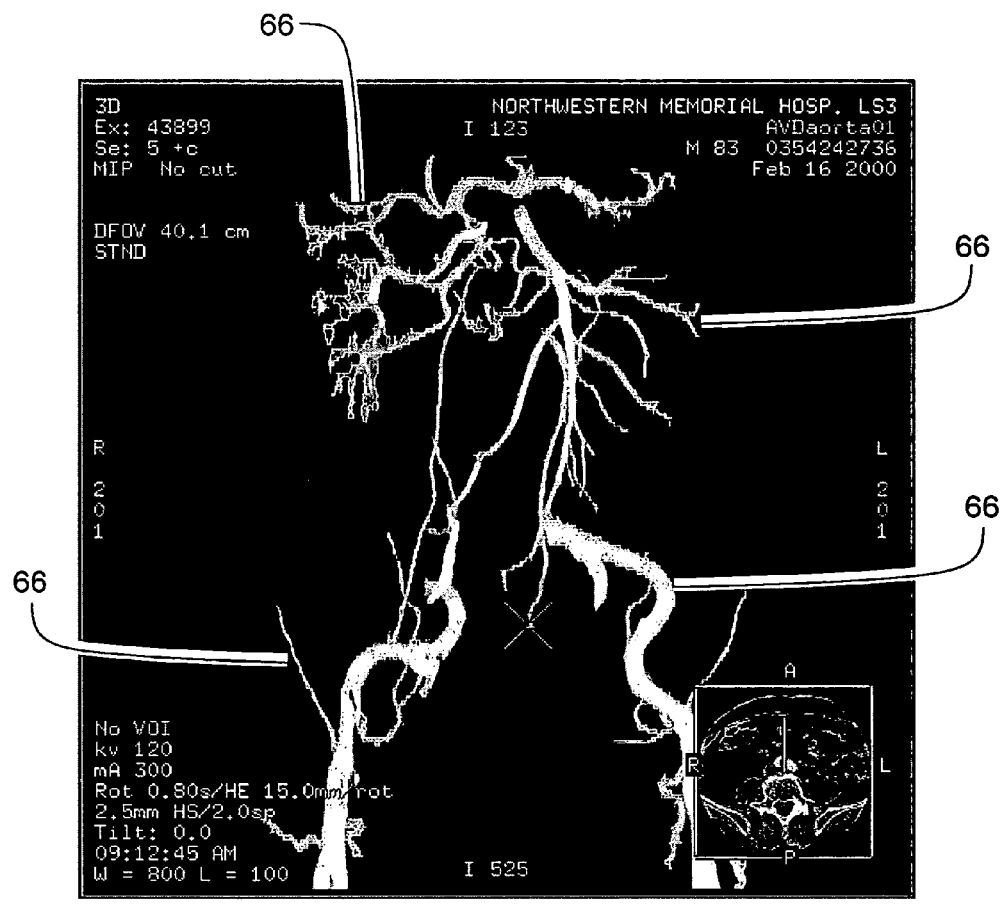
FIG. 7 is an image of branches leaving the main aorta.
Figure 8:
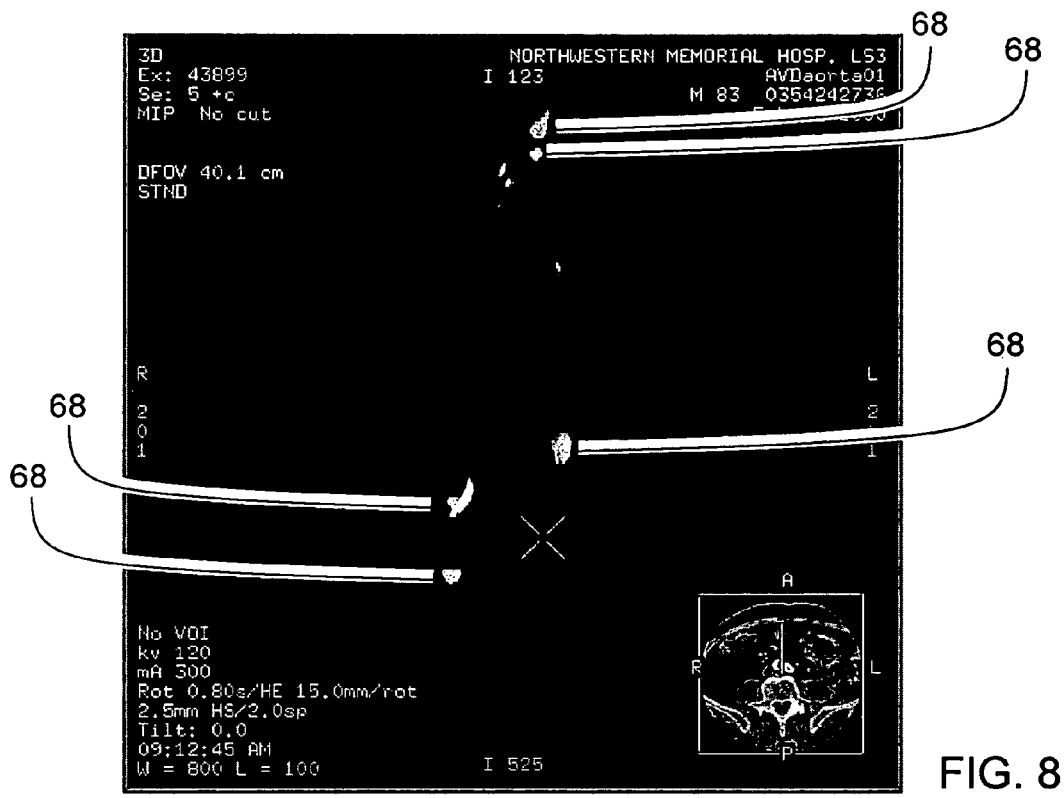
FIG. 8 is an image showing some bifurcation points of the branches of the aorta.
Figure 9:
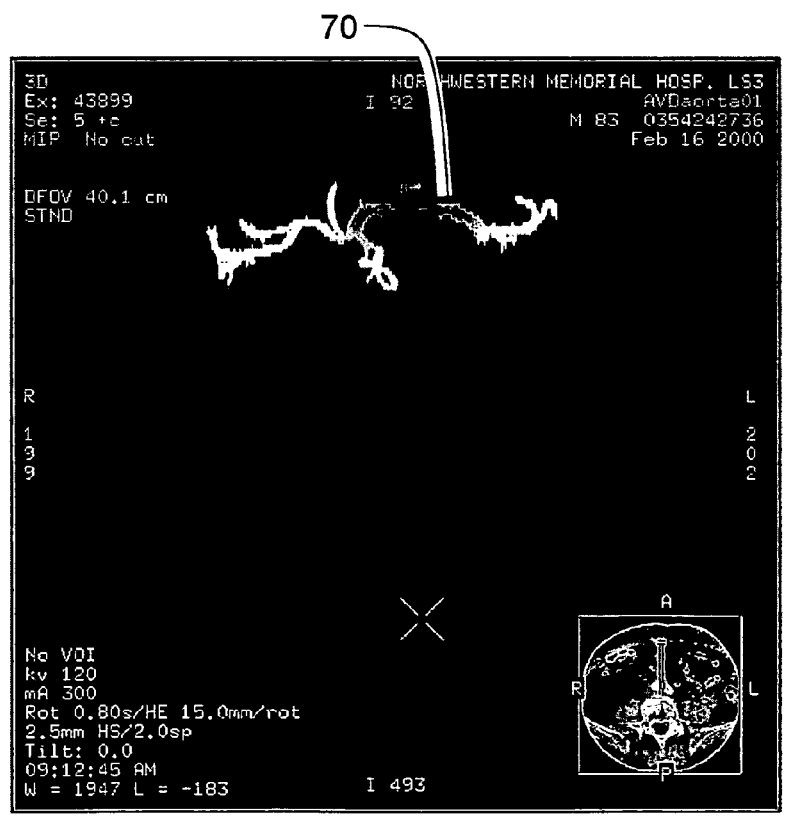
FIG. 9 is a distance map representative of that used in some configurations of the present invention.

Bifurcation points are identified along with branches 66 departing from main aorta 64 are found at step 106. An example of an image of a main aorta 64 is shown in FIG. 6, whereas branches 66 leaving the main aorta (not all of which are labeled) are shown in FIG. 7. Identifications of bifurcation points (such as bifurcation points 68 shown in isolation in FIG. 8) are performed utilizing mathematical morphology techniques and applying a Hessian filter to remove non-vessel-like volumes, such as the kidneys. Next, at step 108, volume analysis routine 103 builds an adjacency graph from each branch 66 coming out of main aorta 64 is built. For example, in some configurations of the present invention, an adjacency graph is generated from a distance map 70 such as that shown in FIG. 9. The point of origin of distance map 70 is a bifurcation point (not necessarily those shown in FIG. 8). The adjacency graph is used as a robust and quick way to represent the characteristics of a volume, and more particularly, vessels. To build the adjacency graph, the software instructs the processor to calculate the distance map of the branch. As a result of this calculation, each node is represented as the points belonging to a range of distances.

Figure 10:
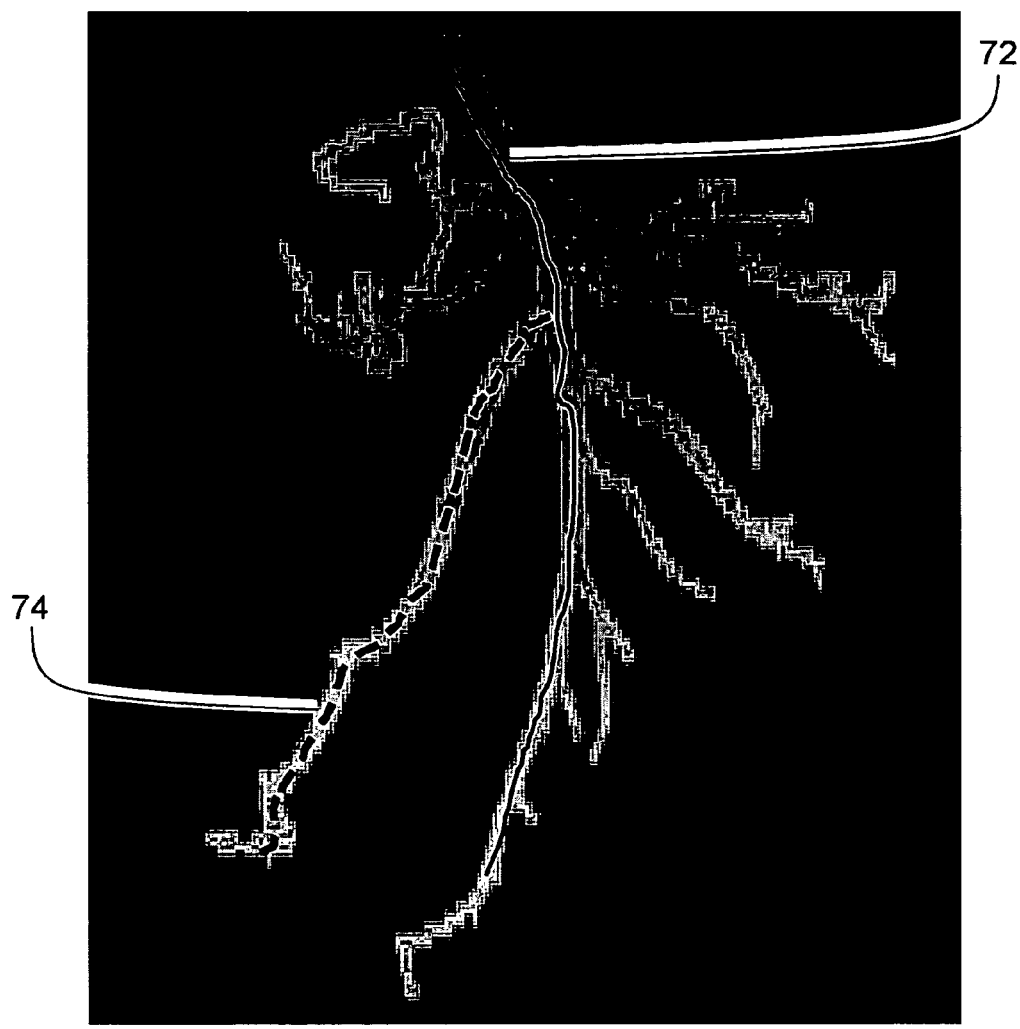
FIG. 10 is an image of an aorta showing an example of a favored path and a less favored path.

Once the adjacency graph is determined, each path joining the initial node and an end node is analyzed. More particularly, at step 110, for the adjacency graph of each branch, the best sub-branch is selected according to its characteristics. Preselected criteria used to choose the best sub-branch include, in some configurations, the diameter of the branch (to best be able to follow the path of a thick branch) and the curvature of the branch (favoring sub branches that have the least tortuosity). For example, and referring to FIG. 10, path 72 would be favored and selected over path 74 in various configurations of the present invention. More particularly, for each path, an average diameter of each node is used to calculate a cumulative diameter. A favored path is path with the highest cumulative diameter. Also, in some configurations of the present invention, for each possible path, the maximum curvature is determined. The average diameter of each node is calculated directly from the number of points in a delta volume and knowing the delta distance. The center of the node is determined as the center of gravity of the delta volume, and the local curvature is calculated using three points (including the center of the node). A favored path is the path having the lowest maximum curvature. In some configurations, the cumulative diameter and maximum curvature are normalized and weighted to determine the most favored or "best" path. This "best" path is indicated visually (e.g., by a colored line) and displayed on a display device in some configurations of the present invention. Preselected criteria are then used to select the best or at least a favorable path.

Figure 11:
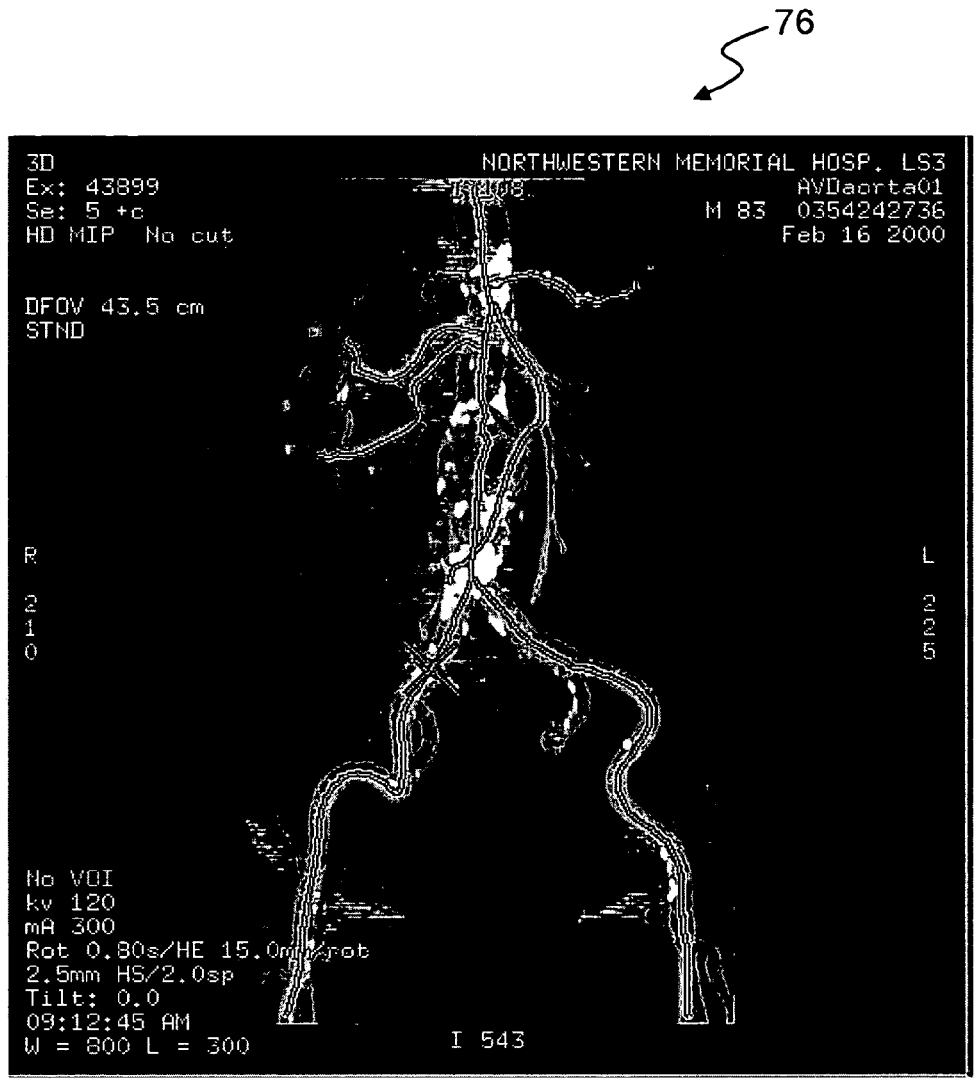
FIG. 11 is a labeled image of an aorta and its branches.

At step 112, the various branches of the aorta are labeled. Software routine 103 is configured to determine the name of each branch using local node orientation and general branch orientation. The orientation of the node is determined in some configurations as a vector joining two consecutive nodes. These orientations are compared to an a priori anatomical model, and the names are determined as a result of this comparison. The labeled image (for example, image 76 of FIG. 11) is displayed at step 114. (In some configurations, the indication of the best path and the labels of the branches image are provided in a single image.) More particularly, in some configurations of the present invention, the local node orientation and the general branch orientation are used to classify the different branches using an a priori anatomical model. For example, in one configuration of the present invention, an anatomical model is used in which renal arteries are essentially horizontal and iliac arteries are more substantially vertical.

Software instructions configured to instruct a processor to perform the processing steps indicated in FIG. 3 and described herein can reside in firmware or other memory of computer 36 and/or on a computer readable medium or media 52. Display 42 can be used to display images to an operator and console 40 can be used by the operator to interact with computer 36, for example, to instruct imaging system 10 to scan a patient 22 to obtain reconstructed image data and/or to initiate volume analysis routine 103. It will also be appreciated that the processes of the present invention can be carried out on a computer system or workstation separate from imaging system 10, as long as data from an imaging system 10 suitable for processing on the separate computer system or workstation are provided.

It will thus be appreciated that configurations of the present invention provide rapid, automated identification and labeling of different branches of a CT image without requiring manual positioning of points. Also, although the present invention has been described in connection with aorta analysis, it will be appreciated that configurations of the present invention are not limited solely to selection and labeling of aorta vessels, nor are they limited to using a particular generation (i.e., technology) CT imaging system (for example, electron beam CT imaging systems can be used). Even other types of imaging systems (e.g., MRI) can be used.

While the invention has been described in terms of various specific embodiments, those skilled in the art will recognize that the invention can be practiced with modification within the spirit and scope of the claims.

What is claimed is:

1. A method for selecting and labeling a vessel image, using a processor enable to compute, said method comprising:

locating an initial point on a main vessel in a bone-free medical image obtained from a medical imaging apparatus;

identifying bifurcation points and branches departing from the main vessel;

building an adjacency graph of each branch coming from the main vessel;

and at least one of:

selecting at least a favorable path through the vessels in accordance with predetermined criteria using the adjacency branch; and labeling branches of the main vessel by comparing local node orientation and general branch orientation to an a priori anatomical model and determining names in accordance with said comparison; and outputting at least one of the selected best or at least a favorable path through the vessels and the labeled branches of the main vessel to using a display device.

2. A method in accordance with claim 1 further comprising:

operating the imaging system to obtain reconstructed image data including a volume having vessels therein; and applying a bone removal routine to the reconstructed image data to produce the bone-free image.

3. A method in accordance with claim 2 wherein said imaging system is a CT imaging system, said volume having vessels therein is a volume including an aorta volume, and said main vessel is the aorta.

4. A method in accordance with claim 3 wherein said operating an imaging system to obtain reconstructed image data further comprises operating the imaging system to obtain a 3D CT abdominal image.

5. A method in accordance with claim 2 wherein said volume having vessels therein is a volume including an aorta volume and said main vessel is the aorta, and further wherein said locating an initial point on a main vessel further comprises utilizing a volume analysis routine to find a highest 2D slice of the aorta and searching for a biggest connected component.

6. A method in accordance with claim 1 wherein said identifying bifurcation points further comprises applying a Hessian filter to remove non-vessel-like volumes.

7. A method in accordance with claim 1 including selecting and displaying a best or at least a favorable path through the vessels, and wherein said selecting and display a best or at least a favorable path further comprises analyzing each path joining an initial node and an end node.

8. A method in accordance with claim 7 wherein the preselected criteria comprise at least one member selected from the group consisting of lowest maximum curvature and highest cumulative diameter.

9. A computer system configured to:

locate an initial point on a main vessel in a bone-free medical image obtained from a medical imaging apparatus;

identify bifurcation points and branches departing from the main vessel;

analyze each path joining an initial node and an end node;

build an adjacency graph of each branch coming from the main vessel;

and at least one of:

select and display at least a favorable path through the vessels in accordance with predetermined criteria using the adjacency branch wherein the preselected criteria comprise at least one member selected from the group consisting of lowest maximum curvature and highest cumulative diameter; and label and display branches of the main vessel.

10. A computer system in accordance with claim 9 controlling a medical imaging device, and further configured to operate the medical imaging device to obtain reconstructed image data including a volume having vessels therein; and said computer or workstation further configured to apply a bone removal routine to the reconstructed image data to produce the bone-free image.

11. A device in accordance with claim 10 wherein said device is a CT imaging system, said volume having vessels therein is a volume including an aorta volume, and said main vessel is the aorta.

12. A device in accordance with claim 11 wherein said reconstructed image data is a 3D CT abdominal image.

13. A device in accordance with claim 10 wherein said volume having vessels therein is a volume including an aorta volume and said main vessel is the aorta, and further wherein to locate an initial point on a main vessel, said device configured to utilize a volume analysis routine to find a highest 2D slice of the aorta and searching for a biggest connected component.

14. A device in accordance with claim 9 wherein to identify bifurcation points, said device configured to apply a Hessian filter to remove non-vessel-like volumes.

15. A computer system in accordance with claim 9 wherein to identify bifurcation points, said computer or workstation configured to apply a Hessian filter to remove non-vessel-like volumes.

16. A computer readable medium having recorded thereon instructions configured to instruct a processor to:

locate an initial point on a main vessel in a bone-free medical image obtained from a medical imaging apparatus;

identify bifurcation points and branches departing from the main vessel;

build an adjacency graph of each branch coming from the main vessel;

and at least one of:

select and display at least a favorable path through the vessels in accordance with predetermined criteria using the adjacency branch wherein the preselected criteria comprise at least one member selected from the group consisting of lowest maximum curvature and highest cumulative diameter; and label and display branches of the main vessel.

17. A medium or media in accordance with claim 16 wherein said instructions configured to instruct a processor to build an adjacency graph further comprise instructions configured to instruct a processor to utilize a distance map to generate the adjacency graph.

* * * * *